(12) United States Patent
Metzger et al.

(10) Patent No.: US 6,723,846 B1
(45) Date of Patent: Apr. 20, 2004

(54) TRIAZINYLAMINOSTILBENE DERIVATIVE AS FLUORESCENT WHITENING AGENTS

(75) Inventors: Georges Metzger, Moernach (FR); Serge Hauger, Ranspach-le-Bas (FR); Fabienne Cuesta, Roppentzwiller (FR); Christophe Bulliard, Basel (CH); Peter Rohringer, Schönenbuch (CH); Marc Roger Grienenberger, Bartenheim (FR)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/070,525

(22) PCT Filed: Sep. 4, 2000

(86) PCT No.: PCT/EP00/08621
§ 371 (c)(1),
(2), (4) Date: Mar. 6, 2002

(87) PCT Pub. No.: WO01/19804
PCT Pub. Date: Mar. 22, 2001

(30) Foreign Application Priority Data

Sep. 10, 1999 (EP) .............................. 99810813

(51) Int. Cl.⁷ ...................... C07D 251/68; C09K 11/06
(52) U.S. Cl. .............................. 544/193.2; 252/301.21; 252/301.23; 427/411; 427/412; 427/158; 8/119; 8/648; 8/919
(58) Field of Search ...................................... 544/193.2

(56) References Cited

U.S. PATENT DOCUMENTS 3,740,341 A 6/1973 Brocklehurst et al. ... 252/301.2

FOREIGN PATENT DOCUMENTS

| DE | 2 335 570 | * | 1/1974 |
| WO | 96/00220 | | 1/1996 |
| WO | WO-96 00221 | * | 1/1996 |
| WO | WO-98 42685 | * | 10/1998 |

* cited by examiner

Primary Examiner—Venkataraman Balasubramanian
(74) Attorney, Agent, or Firm—Kevin T. Mansfield

(57) ABSTRACT

The present invention relates to compounds having formula (1): wherein each $R_1$ represents, independently, a linear $C_1$–$C_4$-alkylene residue which is unsubstituted or substituted by hydroxy, $C_1$–$C_4$-alkyl, $C_1$–$C_4$-alkoxy, $C_1$–$C_4$-hydroxy- or alkoxy-alkoxy, —OCOM, —OCOC$_1$–C$_4$-alkyl, or an amino acid residue from which a hydrogen atom on the amino group has been removed; each $R_2$ represents, independently, a linear $C_1$–$C_4$-alkylene residue which is unsubstituted or substituted by hydroxy, $C_1$–$C_4$-alkyl, $C_1$–$C_4$-alkoxy, $C_1$–$C_4$-hydroxy- or alkoxy-alkoxy, —OCOM, —OCOC$_1$–C$_4$-alkyl, —CO$_2$M, CO$_2$C$_1$–C$_4$-alkyl SO$_3$M or phenoxy which is unsubstituted or substituted by halogen, $C_1$–$C_4$-alkyl or $C_1$–$C_4$-alkoxy, —CO$_2$M or CO$_2$C$_1$–C$_4$-alkyl, NH$_3$ or mono- or disubstituted amino; or phenyl which is unsubstituted or substituted by 1 to 3 SO$_3$M, SO$_2$NHC$_1$–C$_4$-alkyl, —SO$_2$NH$_2$, —CO$_2$M, —CO$_2$M, —CO$_2$C$_1$–C$_4$-alkyl, —CONH$_2$, —CONHC$_1$–C$_4$-alkyl, —NHCOC$_1$–C$_4$-alkyl or mono- or disubstituted amino groups; each $R_3$ represents independently, hydrogen, $C_1$–$C_4$-alkyl, halogen, cyano, SO$_3$M, —SO$_2$NH$_2$, SO$_2$NHC$_1$–C$_4$-alkyl, —CO$_2$M, —CO$_2$C$_1$–C$_4$-alkyl, —CONH$_2$, —CONHC$_1$–C$_4$-alkyl, or —NHCOC$_1$–C$_4$-alkyl; M is hydrogen, an alkali metal atom, ammonium or a cation formed from an amine and m is an integer of 1 to 3, a process for their preparation and use of the compounds as optical brightening agents for synthetic or natural organic materials or for removing stain in photographic materials.

20 Claims, No Drawings

TRIAZINYLAMINOSTILBENE DERIVATIVE AS FLUORESCENT WHITENING AGENTS

The present invention relates to new 4,4'-diaminostilbene-2,2'-disulfonic acid compounds which are useful as fluorescent whitening agents or for removing stain in photographic materials.

In WO 96/00221, there are described optical brightening agents for textiles, paper etc. The disclosed compounds have the formula:

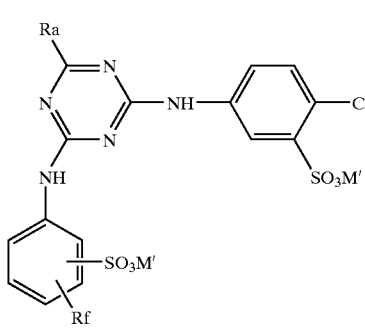

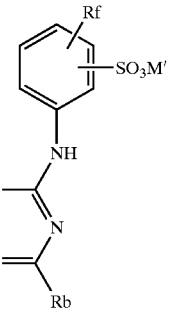

in which $R_a$ and $R_b$ are the same or different and each has the formula —$NR_cR_d$ in which $R_c$ is hydrogen; $C_1$–$C_6$alkyl which is optionally substituted by at least one of mercapto, $C_1$–$C_6$thioalkyl, OH and $SO_3M'$ in which $M'$ is hydrogen, a colourless cation or an amine-derived cation; or —$R_e(CO_2M')_x$ in which $R_e$ is an aliphatic moiety having 1–6 carbon atoms, those valencies not bonded with groups $CO_2M'$ being bonded with at least one of hydrogen, mercapto, $C_1$–$C_6$thioalkyl, OH and $SO_3M'$ in which $M'$ has its previous significance and x is an integer from 1 to 4, provided that, when $R_c$ is $C_1$–$C_6$alkyl which is optionally substituted by at least one of mercapto, $C_1$–$C_6$thioalkyl, OH and $SO_3M'$, $R_c$ is substituted with at least both of OH and $SO_3M'$; $R_d$ is $R_c$, hydrogen or $C_3$–$C_6$alkyl, provided that $R_c$ and $R_d$ cannot both be hydrogen and that, when one of $R_c$ and $R_d$ is hydrogen, the other cannot be —(NHCH$_2$CO$_2$H); or $R_c$ and $R_d$, together with the nitrogen atom, form a ring having from 5–6 members only, one of which is heterocyclic, which ring is singly substituted with —COOM' or —$SO_3M'$; and each $R_f$, independently, is hydrogen, methyl, $C_1$–$C_6$alkoxy or halogen.

Furthermore, WO 98/42685 describes similar compounds having the formula:

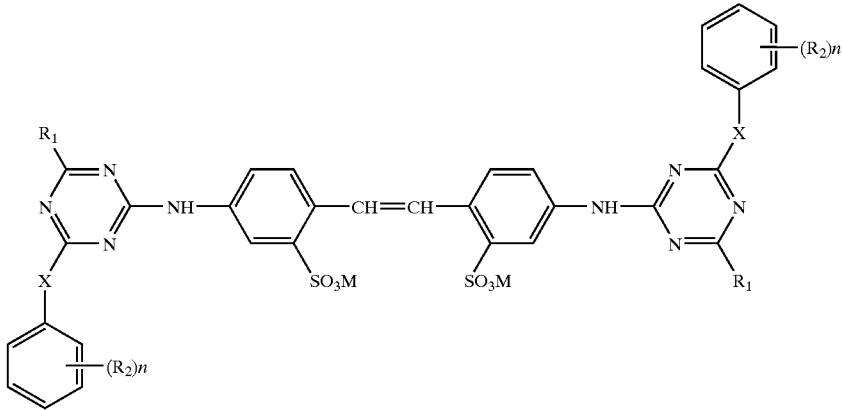

in which X is O or, preferably, NH; M is hydrogen, an alkali metal atom, ammonium or a cation formed from an amine; each $R_1$, independently, is an amino acid residue from which a hydrogen atom on the amino group has been removed; n is 1 or 2; and each $R_2$, independently, is hydrogen, $C_1$–$C_3$alkyl, halogen, cyano, COOR in which R is hydrogen or $C_1$–$C_3$alkyl, CONH—R in which R has its previous significance, $SO_2NH$—R in which R has its previous significance, NH—COR in which R has its previous significance, $SO_3M$ in which M has its previous significance or, when n is 1, $R_2$ can also be CO—$R_3$ in which $R_3$ is $C_1$–$C_3$alkyl or phenyl, certain compounds being excluded, and their use as fluorescent whitening agents.

A new class of 4,4'-diaminostilbene-2,2'-disulfonic acid compounds has now been found most of which are useful as fluorescent whitening agents and which have superior properties to, and are more readily prepared than the compounds disclosed in WO 96/00221 and in WO 98/42685. Furthermore, the new compounds are useful for removing stain in photographic materials.

Accordingly, the present invention provides new compounds having the formula:

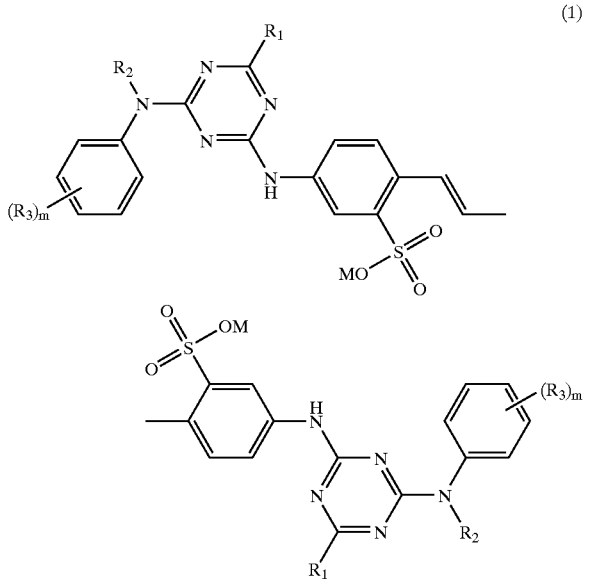

(1)

wherein each $R_1$ represents, independently, a linear $C_1$–$C_4$-alkylene residue which is unsubstituted or substituted by hydroxy, $C_1$–$C_4$-alkyl, $C_1$–$C_4$-alkoxy, $C_1$–$C_4$-hydroxy- or alkoxy-alkoxy, —OCOM, —OCOC$_1$–$C_4$-alkyl, or an amino acid residue from which a hydrogen atom on the amino group has been removed; each $R_2$ represents, independently, a linear $C_1$–$C_4$-alkylene residue which is unsubstituted or substituted by hydroxy, $C_1$–$C_4$-alkyl, $C_1$–$C_4$-alkoxy, $C_1$–$C_4$-hydroxy- or alkoxy-alkoxy, —OCOM, —OCOC$_1$–$C_1$–$C_4$alkyl, —CO$_2$M, CO$_2$C$_1$–$C_4$-alkyl SO$_3$M or phenoxy which is unsubstituted or substituted by halogen, $C_1$–$C_4$-alkyl or $C_1$–$C_4$-alkoxy, —CO$_2$M or —CO$_2$C$_1$–$C_4$-alkyl, NH$_2$ or mono- or disubstituted amino; or phenyl which is unsubstituted or substituted by 1 to 3 SO$_3$M, SO$_2$NHC$_1$-$C_4$-alkyl, —SO$_2$NH$_2$, —CO$_2$M, —CO$_2$C$_1$–$C_4$-alkyl —CONH$_2$, —CONHC$_1$–$C_4$-alkyl, —NHCOC$_1$–$C_4$-alkyl or mono- or disubstituted amino groups; each $R_3$ represents, independently, hydrogen, $C_1$–$C_4$-alkyl, halogen, cyano, SO$_3$M, —SO$_2$NH$_2$, SO$_2$NHC$_1$–$C_4$-alkyl, —CO$_2$M, —CO$_2$C$_1$–$C_4$-alkyl, —CONH$_2$, —CONHC$_1$–$C_4$-alkyl, or —NHCOC$_1$–$C_4$-alkyl;

M is hydrogen, an alkali metal atom, ammonium or a cation formed from an amine and m is an integer of 1 to 3.

Within the scope of the compounds of formula (1) both of the $R_1$ groups, the $R_2$ groups and the $R_3$ groups are preferably identical.

Further preferred compounds of formula (1) are those in which each of the amino acid residues $R_1$ is the same and each has the formula —NH—CH(CO$_2$H)—$R_4$ in which $R_4$ is hydrogen or a group having the formula —CHR$_5$R$_6$ in which $R_5$ and $R_6$, independently, are hydrogen or $C_{1-4}$-alkyl optionally substituted by one or two substituents selected from hydroxy, thio, methylthio, amino, carboxy, sulfo, phenyl, 4-hydroxyphenyl, 3,5-diiodo-4-hydroxyphenyl, β-indolyl, β-imidazolyl and NH=C(NH$_2$)NH—.

Particularly useful compounds of formula (1) are those in which the amino acid from which the amino acid residues $R_1$ are derived is glycine, alanine, sarcosine, serine, cysteine, phenylalanine, tyrosine (4-hyroxyphenylalanine), diiodotyrosine, tryptophan (β-indolyalanine), histidine ((β-imidazolylalanine), α-aminobutyric acid, methionine, valine (α-aminoisovaleric acid), norvaline, leucine (α-aminoisocaproic acid), isoleucine (α-amino-β-methylvaleric acid), norleucine (α-amino-n-caproic acid), arginine, ornithine (α,δ-diaminovaleric acid), lysine (α,ε-diaminocaproic acid), aspartic acid (aminosuccinic acid), glutamic acid (α-aminoglutaric acid), threonine, hydroxyglutamic acid or taurine, or a mixture or an optical isomer thereof.

Especially preferred compounds are those in which the amino acid from which the amino acid residues $R_1$ are derived is sarcosine, taurine, glutamic acid or aspartic acid, aspartic acid or iminodiacetic acid being the most desirable.

Further preferred compounds of formula (1) are those in which $R_1$ is a linear $C_1$–$C_4$-alkylene residue which is unsubstituted or substituted by hydroxy, $C_1$–$C_4$-alkyl, $C_1$–$C_4$-alkoxy, $C_1$–$C_4$-hydroxy- or alkoxy-alkoxy, —OCOM, —OCOC$_1$–$C_4$-alkyl, especially those in which $R_1$ is a linear $C_1$–$C_4$-alkylene residue which is unsubstituted or substituted by hydroxy, $C_1$–$C_4$-alkyl, $C_1$–$C_4$-alkoxy, $C_1$–$C_4$-hydroxy- or alkoxy-alkoxy and, most preferably, those in which $R_1$ is a linear $C_1$–$C_4$-alkylene residue which is substituted by hydroxy or $C_1$–$C_4$-alkoxy, M being as previously defined.

With regard to the residue $R_2$, this is preferably a linear $C_1$–$C_4$-alkylene residue which is unsubstituted or substituted by hydroxy, $C_1$–$C_4$-alkyl, $C_1$–$C_4$-alkoxy, $C_1$–$C_4$-hydroxy or alkoxy-alkoxy, —OCOM, —OCOC$_1$–$C_4$-alkyl, —CO$_2$M, —CO$_2$C$_1$–$C_4$-alkyl, SO$_3$M, phenoxy which is unsubstituted or substituted by halogen, $C_1$–$C_4$-alkyl, $C_1$–$C_4$-alkoxy, —CO$_2$M or —CO$_2$C$_1$–$C_4$-alkyl, NH$_2$ or mono- or disubstituted amino, most preferably, a methylene, ethylene or propylene residue which is substituted by hydroxy, $C_1$–$C_4$-alkyl, $C_1$–$C_4$-alkoxy, $C_1$–$C_4$-hydroxy- or alkoxy-alkoxy, —OCOM, —OCOC$_1$–$C_4$-alkyl, —CO$_2$M, —CO$_2$C$_1$–$C_4$-alkyl, SO$_3$M or di-$C_1$–$C_4$-alkylamino.

Compounds of particular interest are those in which $R_2$ is hydoxyethyl, hydroxypropyl, ethoxyethyl, hydroxyethoxyethyl, methoxyethoxyethyl, an acetic or propionic acid residue or methyl or ethyl esters thereof, an ethyl or methyl acetate, dimethylaminoethyl or ethyl sulphonic acid or the sodium salt thereof, an hydoxyethyl or a sodium acetate residue being most preferred.

Further interesting compounds are those in which each $R_2$ is phenyl which is unsubstituted or substituted by 1 to 3 SO$_3$M, SO$_2$NHC$_1$–$C_4$-alkyl, —SO$_2$NH$_2$, —CO$_2$M, —CO$_2$C$_1$–$C_4$-alkyl, —CONH$_2$, —CONHC$_1$–$C_4$-alkyl, —NHCOC$_1$–$C_4$-alkyl or mono- or disubstituted amino groups.

Of especial interest are compounds in which each $R_2$ is phenyl which is unsubstituted or substituted by one SO$_3$M, —SO$_2$NH$_2$ or —NHCOC$_1$–$C_4$-alkyl group, however, the phenyl group is preferably unsubstituted.

Further preferred compounds of formula (1) are those in which each $R_3$ residue represents hydrogen, $C_1$–$C_4$-alkyl, halogen, cyano, SO$_3$M, —SO$_2$NH$_2$, SO$_2$NHC$_1$–$C_4$-alkyl, —CO$_2$M, —CO$_2$C$_1$–C$_4$-alkyl, —CONH$_2$, —CONHC$_1$–C$_4$-alkyl, or —NHCOC$_1$–C$_4$-alkyl, those in which R$_3$ represents hydrogen being most preferred.

In the formulae of the above compounds, M is preferably hydrogen, Na, K, Ca, Mg, ammonium, mono-, di-, tri- or tetra-C$_1$–C$_4$alkylammonium, mono-, di- or tri-C$_1$–C$_4$-hydroxyalkylammonium or ammonium that is di- or tri-substituted with a mixture of C$_1$–C$_4$-alkyl and C$_1$–C$_4$-hydroxyalkyl groups, especially hydrogen or Na and m is preferably 1.

Compounds of most particular interest are those of the formula:

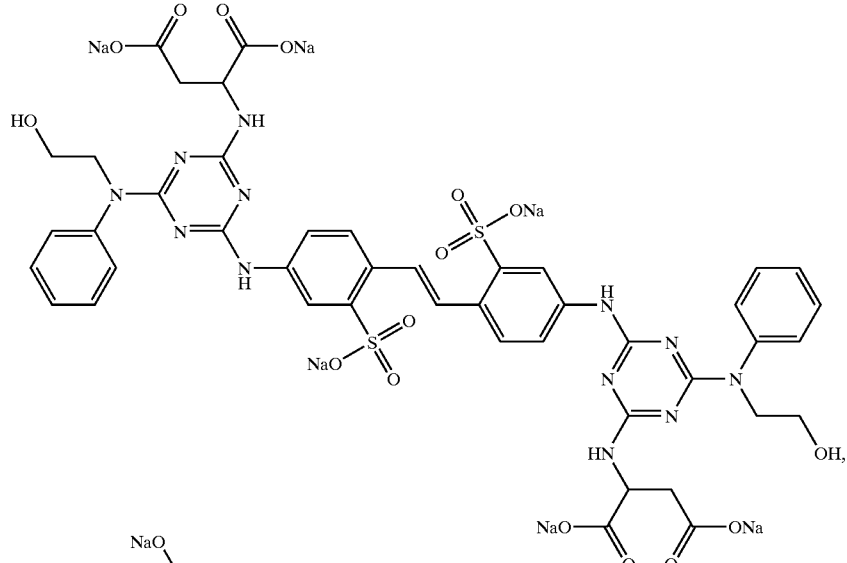

(2)

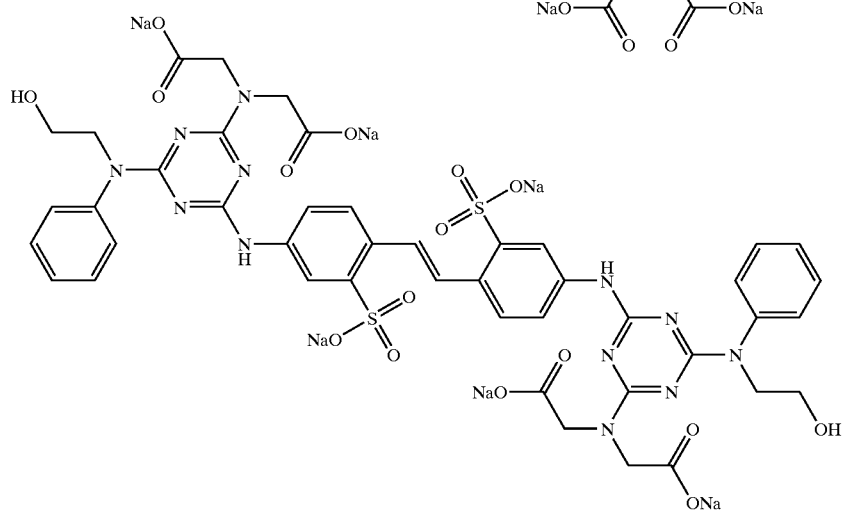

(3)

and

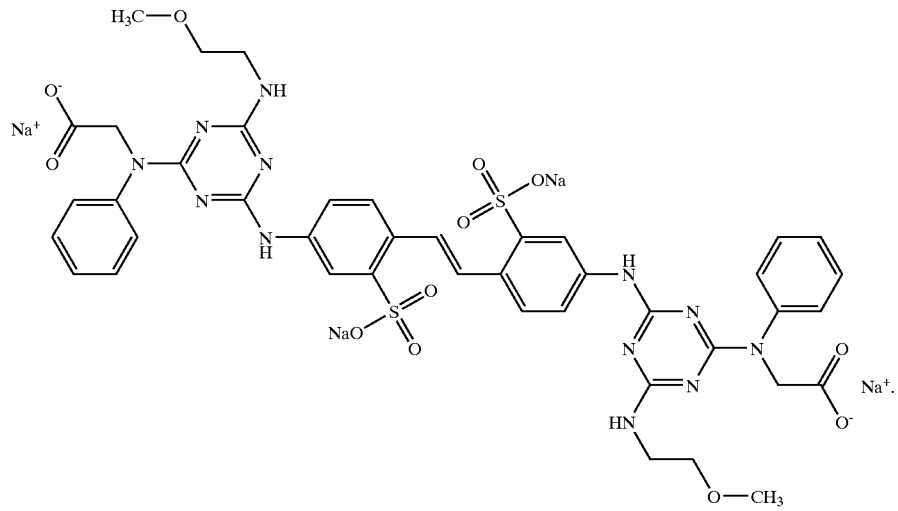

(4)

The compounds of formula (1) may be produced by reacting, under known reaction conditions, cyan uric chloride, successively, in any desired sequence, with each of 4,4'-diamino-2,2'-stilbene disulfonic acid, an amino compound capable of introducing a group

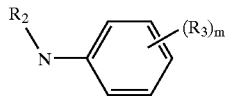

in which $R_2$, $R_3$ and m have their previous significance, and a compound capable of introducing a group $R_1$, in which $R_1$ has its previous significance.

Preferably, 2 males of cyanuric chloride are initially reacted with 1 mole of 4,4'-diamino-2,2'-disulfonic acid, then with an amino compound capable of introducing a group

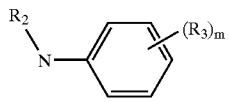

in which $R_2$, $R_3$ and m have their previous significance, and, finally, with a compound capable of introducing a group $R_1$, in which $R_1$ has its previous significance.

Consequently, a further aspect of the invention is a compound of formula:

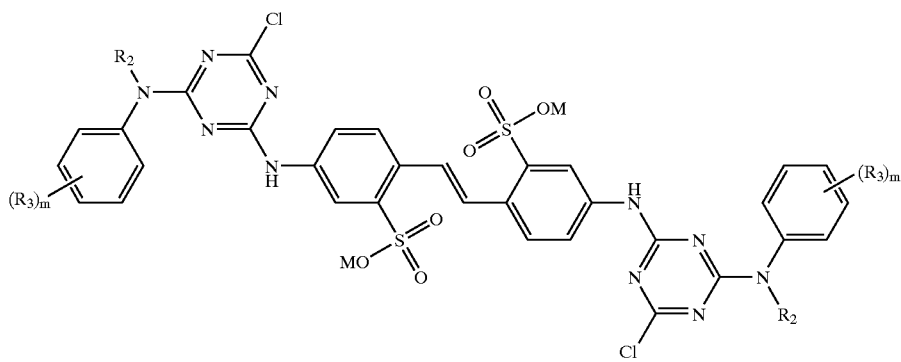

(5)

in which $R_2$, $R_3$, M and m are as previously defined.

Within the scope of the compounds of formula (5) both of the two $R_2$ groups and the two $R_3$ groups are preferably identical.

With regard to the residue $R_2$, this is preferably a methylene, ethylene or propylene residue which is substituted by hydroxy, $C_1$–$C_4$-alkyl, $C_1$–$C_4$-alkoxy, $C_1$–$C_4$-hydroxy- or alkoxy-alkoxy, —OCOM, —OCOC$_1$–C$_4$-alkyl, —CO$_2$M, —CO$_2$C$_1$–C$_4$-alkyl, SO$_3$M or di-C$_1$–C$_4$-alkylamino.

Compounds of particular interest are those in which $R_2$ is hydoxyethyl, hydroxypropyl, ethoxyethyl, hydroxyethoxyethyl, methoxyethoxyethyl, an acetic or prop ionic acid residue or methyl or ethyl esters thereof, an ethyl or methyl acetate, dimethylaminoethyl or ethyl sulphonic acid or the sodium salt thereof, hydoxyethyl or a sodium acetate residue being, most preferred.

Further interesting compounds are those in which each $R_2$ is phenyl which is unsubstituted or substituted by 1 to 3 SO$_3$M, SO$_2$NHC$_1$–C$_4$-alkyl, —SO$_2$NH$_2$, —CO$_2$M, —CO$_2$C$_1$–C$_4$-alkyl, CONH$_2$, —CONHC$_1$–C$_1$-alkyl, —NHCOC$_1$–C$_4$-alkyl or mono- or disubstituted amino groups.

Of especial interest are compounds in which each $R_2$ is phenyl which is unsubstituted or substituted by one SO$_3$M, —SO$_2$NH$_2$ or —NHCOC$_1$–C$_4$-alkyl group, however, the phenyl group is preferably unsubstituted.

Further preferred compounds of formula (5) are those in which each $R_3$ residue represents hydrogen, $C_1$–$C_4$-alkyl, halogen, cyano, SO$_3$M, —SO$_2$NH$_2$, SO$_2$NHC$_1$–C$_4$-alkyl, —CO$_2$M, —CO$_2$C$_1$–C$_4$-alkyl, —CONH$_2$, —CONHC$_1$–C$_4$-alkyl, or —NHCOC$_1$–C$_4$-alkyl, those in which $R_3$ represents hydrogen being most preferred.

In the formulae of the above compounds, M is preferably hydrogen, Na, K, Ca, Mg, ammonium, mono-, di-, tri- or tetra-$C_1$–$C_4$alkylammonium, mono-, di- or tri-$C_1$–$C_4$-hydroxyalkylammonium or ammonium that is di- or tri-substituted with a mixture of $C_1$–$C_4$-alkyl and $C_1$–$C_4$-hydroxyalkyl groups, especially hydrogen or Na and m is preferably 1.

The starting materials are known compounds which are readily available.

A further aspect of the invention is a composition for whitening synthetic or natural organic materials or for removing stain from photographic materials, which contains water, a fluorescent whitening agent of formula (1) and, optionally, auxiliaries.

More specifically, such brightener compositions contain water and, in each case based on the weight of the formulation, from 3 to 25% by weight, preferably from 5 to 15% by weight of the above defined fluorescent whitening agent mixture and also 0 to 60%, preferably 5 to 50% by weight, of auxiliaries.

Suitable auxiliaries include, for example, anionic or non-ionic dispersants from the class of ethylene oxide adducts with fatty alcohols, higher fatty acids or alkyl phenols or ethylenediamine ethylene oxide-propylene oxide adducts, copolymers of N-vinylpyrrolidone with 3-vinylpropionic acid, water retention aids, such as ethylene glycol, glycerol or sorbitol, or biocides.

Most of the compounds of formula (1) are excellent fluorescent whitening agents for synthetic or natural substrates such as textiles and, in particular, for paper and also in detergent compositions.

Accordingly, the present invention further provides a method for the fluorescent whitening of a substrate comprising contacting the substrate with a compound having the formula (1).

When used for the fluorescent whitening of paper, the compound of formula (1) according to the present invention may be applied to the paper substrate in the form of a paper coating composition, or directly in the size press.

In one preferred aspect, the present invention provides a method for the fluorescent whitening of a paper surface, comprising contacting the paper surface with a coating composition comprising a white pigment; a binder dispersion; optionally a water-soluble co-binder; and sufficient of a fluorescent whitening agent having the formula (1) according to the present invention, to ensure that the treated paper contains 0.01 to 1% by weight, based on the white pigment, of a fluorescent whitening agent having the formula (1).

As the white pigment component of the paper coating composition used according to the method of the present invention, there are preferred inorganic pigments, e.g., aluminium or magnesium silicates, such as China clay and kaolin and, further, barium sulfate, satin white, titanium dioxide, calcium carbonate (chalk) or talcum; as well as white organic pigments.

The paper coating compositions used according to the method of the present invention may contain, as binder, inter alia, plastics dispersions based on copolymers of butadiene/styrene, acrylonitrile/butadiene/styrene, acrylic acid esters, acrylic acid esters/styrene/acrylonitrile, ethylene/vinyl chloride and ethylene/vinyl acetate; or homopolymers, such as polyvinyl chloride, polyvinylidene chloride, polyethylene and polyvinyl acetate or polyurethanes. A preferred binder consists of styrene/butyl acrylate or styrene/butadiene/acrylic acid copolymers or styrene/butadiene rubbers. Other polymer latices are described, for example, in U.S. Pat. Nos. 3,265,654, 3,657,174, 3,547,899 and 3,240,740.

The optional water-soluble protective colloid may be, e.g., soya protein, casein, carboxymethylcellulose, natural or modified starch, chitosan or a derivative thereof or, especially, polyvinyl alcohol. The preferred polyvinyl alcohol protective colloid component may have a wide range of saponification levels and molecular weights, e.g. a saponification level ranging from 40 to 100; and an average molecular weight ranging from 10,000 to 100,000.

Recipes for coating compositions for paper are described, for example, in J. P. Casey "Pulp and Paper"; Chemistry and Chemical Technology, 2nd edition, Volume III, pages1684–1649 and in "Pulp and Paper Manufacture", 2nd and 5th edition, Volume II, page497 (McGraw-Hill).

The paper coating compositions used according to the method of the present invention preferably contain 10 to 70% by weight of a white pigment. The binder is preferably used in an amount which is sufficient to make the dry content of polymeric compound up to 1 to 30% by weight, preferably 5 to 25% by weight, of the white pigment. The amount of fluorescent brightener preparation used according to the invention is calculated so that the fluorescent brightener is preferably present in amounts of 0.01 to 1% by weight, more preferably 0.05 to 1% by weight, and especially 0.05 to 0.6% by weight, based on the white pigment.

The paper coating composition used in the method according to the invention can, be prepared by mixing the components in any desired sequence at temperature from 10 to 100° C., preferably 20 to 80° C. The components here also include the customary auxiliaries which can be added to regulate the Theological properties, owl such as viscosity or water retention capacity, of the coating compositions. Such auxiliaries are, for example, natural binders, such as starch, casein, protein or gelatin, cellulose ethers, such as carboxyalkylcellulose or hydroxyalkylcellulose, alginic add, alginates, polyethylene oxide or polyethylene, oxide alkyl ethers, copolymers of ethylene oxide and propylene oxide, polyvinyl alcohol, water-soluble condensation products of formaldehyde with urea or melamine, polyphosphates or polyacrylic acid salts.

The coating composition used according to the method of the present invention is preferably used to produce coated printed or writing paper, or special papers such as cardboard or photographic papers.

The coating composition used according to the method of the invention can be applied to the substrate by any conventional process, for example with an air blade, a coating blade, a roller, a doctor blade or a rod, or in the size press, after which the coatings are dried at paper surface temperatures in the range from 70 to 200° C., preferably 90 to 130° C., to a residual moisture content of 3–8%, for example with infra-red driers and/or hot-air driers. Comparably high degrees of whiteness are thus achieved even at low drying temperatures.

By the use of the method according to the invention, the coatings obtained are distinguished by optimum distribution of the dispersion fluorescent brightener over the entire surface and by an increase in the level of whiteness thereby achieved, by a high fastness to light and to elevated temperature (e.g. stability for 24 hours at 60–100° C.) and excellent bleed-fastness to water.

In a second preferred aspect, the present invention provides a method for the fluorescent whitening of a paper surface comprising contacting the paper in the size press with an aqueous solution containing a size, optionally an inorganic or organic pigment and 0.1 to 20 g/l of a fluorescent whitening agent having the formula (1). Preferably, the size is starch, a starch derivative or a synthetic sizing agent, especially a water-soluble copolymer.

In a third preferred aspect, the brighteners defined above are of particular importance for the treatment of textile fabrics. The treatment of textile substrates is advantageously carried out in an aqueous medium in which the particular optical brighteners are present in a finely divided form (suspensions, so-called microdispersions and in some cases solutions). Dispersing agents, stabilisers, wetting agents and further auxiliaries can optionally be added during the treatment.

The treatment is usually carried out at temperatures of from about 20° to 140° C., for example at the boiling point of the bath, or in the region thereof (about 90° C.). For the finishing, according to the invention, of textile substrates it is also possible to use solutions or emulsions in organic solvents, as are used in dyeing practice in so-called solvent dyeing (pad-thermofix method and the exhaustion dyeing process in dyeing machines).

The optical brighteners which can be used according to the present invention can also be employed, for example, in the following use forms:

(a) In mixtures with so-called "carriers", wetting agents, softeners, swelling agents, antioxidants, light stabilisers, heat stabilisers and chemical bleaching agents (chlorite bleach and bleaching bath additives).

(b) In mixtures with crosslinking agents and finishing agents (for example starch or synthetic finishing agents) and also in combination with very diverse textile finishing processes, especially synthetic resin finishes (for example crease resistant finishes such as "wash-and-wear", permanent press and "no-iron"), and also flame resistant finishes, soft handle finishes, anti-soiling finishes or anti-static finishes or antimicrobial finishes.

(c) As additives to various soaps and washing agents.

(d) In combination with other substances having an optical brightening action.

If the brightening process is combined with textile treatment or finishing methods, the combined treatment can in many cases advantageously be effected with the aid of corresponding stable formulations which contain the compounds having an optical. brightening action in a concentration such that the desired brightening effect is obtained.

In certain cases, the full effect of the brightener is achieved by an after-treatment. This can be, for example, a chemical treatment (for example acid treatment), a thermal treatment (for example heat) or a combined chemical/heat treatment.

The amount of the optical brighteners to be used according to the invention, relative to the material to be optically brightened, can vary within wide limits. A distinct and durable effect can already be achieved with vary small amounts and in certain cases, for example, with amounts of 0.03% by weight. However amounts of up to about 0.5% by weight can also be used. For most cases of interest in practice, amounts of between 0.05 and 0.5% by weight relative to the material to be brightened, are preferably of interest.

In a fourth aspect of the invention, the optical brighteners are also especially suitable as additives for washing baths or to industrial and household washing agents and they can be added in various ways. They are appropriately added to washing baths in the form of their solutions in water or organic solvents or also in a state of fine division as aqueous dispersions or slurries. They, or their components, are advantageously added to household or industrial washing agents at any phase of the manufacturing process of the washing agent, for example to the so-called "slurry" prior to spray-drying of the washing powder or during the preparation of liquid washing agent combinations. The compounds can be added both in the form of a solution or dispersion in water or other solvents and also without auxiliaries in the form of a dry brightener powder. However, they can also be sprayed, in the dissolved or pre-dispersed form, onto the finished washing agent.

Washing agents which can be used are the known mixtures of detergent substances, such as, for example, soap in the form of chips and powders, synthetic products, soluble salts of sulphonic acid half-esters of higher fatty alcohols, arylsulphonic acids, which are substituted by higher alkyl and/or polysubstituted by alkyl, carboxylic acid esters with alcohols of medium to higher molecular weight, fatty acid acylaminoalkyl- or aminoaryl-glycerol-sulphonates, phosphoric acid esters of fatty alcohols and the like. So-called "builders" which can be used are, for example, alkali metal polyphosphates and alkali metal polymeta-phosphates, alkali metal pyrophosphates, alkali metal salts of carboxyethylcellulose and other "soil redepositon inhibitors", and also alkali metal silicates, alkali metal carbonates, alkali metal borates, alkali metal perborates, nitrilotriacetic acid, ethylenediamine-tetraacetic acid and foam stabilisers, such as alkanolamides of higher fatty acids. Furthermore, the washing agents can contain, for example: antistatic agents, superfatting skin protection agents, such as lanolin, enzymes, antimicrobial agents, perfumes and dyestuffs.

The brighteners have the particular advantage that they are also effective in the presence of A active chlorine donors, such as, for example, hypochlorite and can be used without substantial loss of the effects in washing baths with non-ionic washing agents, for example alkylphenol polyglycol ethers. Also in the presence of perborate or peracids and activators, for example tetraacetylglycoluril or ethylenediamine-tetraacetic acid are the new brighteners very stable both in pulverulent washing agent and in washing baths.

The brighteners according to the invention are added in amounts of 0.005 to 2% or more and preferably of 0.03 to 0–5%, relative to the weight of the liquid or pulverulent ready-to-use washing agent. When they are used to wash textiles made of cellulose fibres, polyamide fibres, cellulose fibres with a high grade finish, wool and the like, wash liquors which contain the indicated amounts of the optical brighteners according to the invention impart a brilliant appearance in daylight.

The washing treatment is carried out, for example, as follows:

The indicated textiles are treated for 1 to 30 minutes at 5° to 100° C. and preferably at 25° to 100° C. in a wash bath which contains 1 to 10 g/kg of a composite washing agent containing builders and 0.05 to 1% relative to the weight of the washing agent, of the brighteners claimed. The liquor ratio can be 1:3 to 1:50. After washing, the textiles are rinsed and dried in the customary manner. The wash bath can contain, as a bleach additive, 0.2 g/l of active chlorine (for example in the form of hypochlorite) or 0.1 to 2 g/l of sodium perborate.

The brighteners according to the invention can also be applied from a rinsing bath with a "carrier". For this purpose the brightener is incorporated in a soft rinsing agent or in another rinsing agent, which contains, as the "carrier", for example, polyvinyl alcohol, starch, copolymers on an acrylic basis or formaldehyde/urea or ethylene-urea or propylene-urea derivatives, in amounts of 0.005 to 5% or more and preferably of 0.2 to 2%, relative to the rinsing agent. When used in amounts of 1 to 100 ml, and preferably of 2 to 25 ml, per liter of rinsing bath, rinsing agents of this type, which contain the brighteners according to the invention, impart brilliant brightening effects to very diverse types of treated textiles.

In a fifth aspect of the invention, the compounds of formula (1) are also suitable for removing stain in a photographic material which comprises a silver halide photographic light-sensitive material and, more detailedly, to a process thereof, wherein the improvement is made on the prevention of a colour stain and particularly the prevention of a colour dye stain caused in the course of processing said silver halide photographic light-sensitive material by a colour developer and a bleach-fix bath.

The following Examples serve to illustrate the invention; parts and percentages are by weight, unless otherwise stated.

EXAMPLE 1

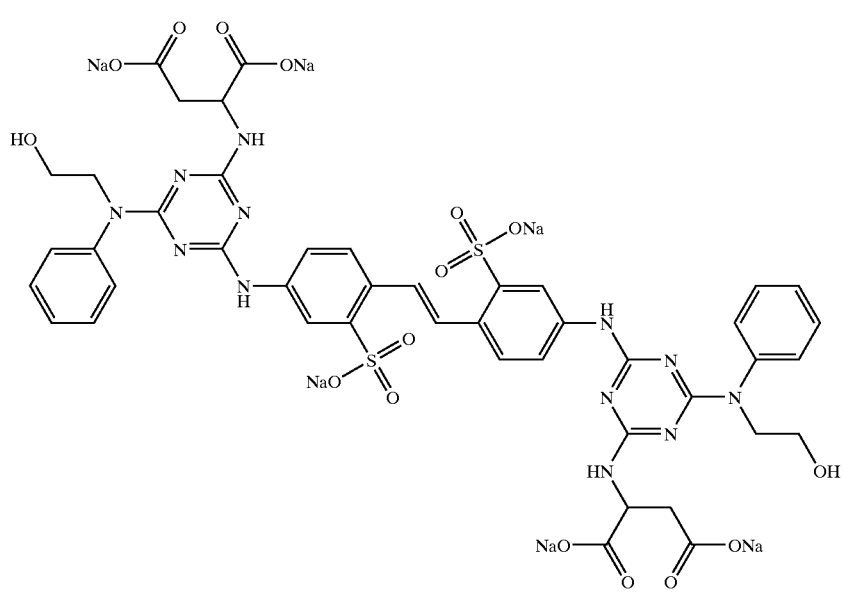

(2)

18.4 g. of cyanuric chloride are dissolved in 100 ml. of acetone and the solution added to 100 g. of ice contained in a reaction vessel. A solution of 18.4 g. of 4,4'-diamino-2,2'-stilbene disulphonic acid sodium salt in 330 ml. of water is then added over 10 minutes at 5° C. 50 ml. of a 1 molar aqueous solution of sodium carbonate are then added over 10 minutes. 14.55 g. of N-2-hydroxyethyl aniline are then added, the temperature raised to 35° C., whereby the pH is maintained between 7 and 7.5, and the mixture stirred for a further 2 hours. The precipitated product is filtered, washed with water and dried to yield 39 g of a compound of formula:

To 10 g. of the compound of formula (2a) in 150 ml. of water, 3.4 g. of aspartic acid are added and the mixture heated to 70° C., the pH being maintained at between 8 and 8.5 by the addition of a 32% aqueous sodium hydroxide solution. After 2 hours at this temperature, the reaction is completed. The pH of the mixture is then adjusted to 3 by the addition of 37% aqueous hydrochloric acid, the temperature being maintained at 70° C. The precipitated free acid is filtered, suspended in a methanol/water mixture and the pH adjusted to 9 by the addition of a 32% aqueous sodium hydroxide solution. The precipitated product is filtered and dried to yield 8.8 g. of the compound of formula (2).

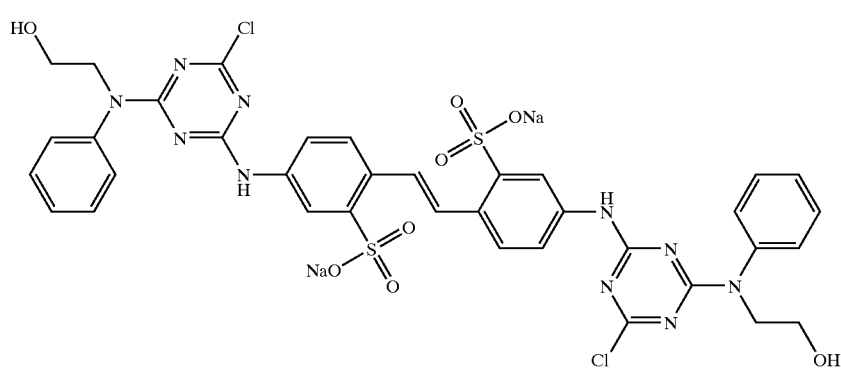

(2a)

Analysis for $C_{36}H_{30}Cl_2N_{10}Na_2O_6S_2$: calculated: C 47.32%, H 3.54%, Cl 7.76%, N 15.33%, S 7.02%; found: C 47.1%, H 4.0%, Cl 7.7%., N 15.5%, S 6.7%.

Analysis for $C_{44}H_{38}N_{12}Na_6O_{16}S_2.10.5H_2O$: calculated: C 38.23%, H 4.31%, N 12.17%, Na 9.99%, S 4.64%; found: C 38.2%, H 4.5%, N 12.2%, Na 9.8%, S 4.6%.

EXAMPLE 2

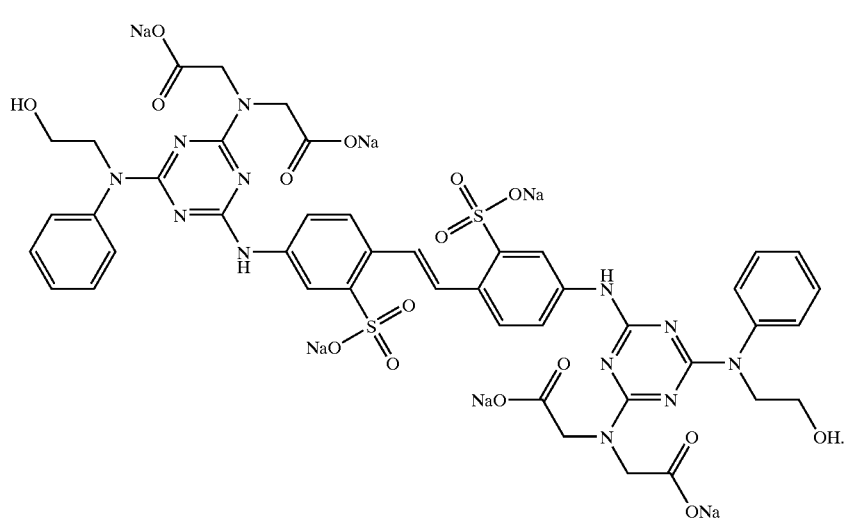
(3)

To 40 g. of ice/water, 12.5 g. of cyanuric chloride are added, followed by 0.5 g. of polyethylene glycol and the mixture stirred for 15 minutes. A solution of 12 g. of 4,4'-diamino-2,2'-stilbene disulphonic acid sodium salt in 90 ml. of water is then added over 10 minutes at 5° C. 20 g. of a 17% aqueous solution of sodium carbonate in 60 ml. of water are then added and the mixture stirred at 5° C. until the pH falls to 5.5. The contents of the flask are then concentrated under vacuum to a weight of 193 g., whereby a 20% solution of compound (2a) results which, according to HPLC, is identical to that obtained in Example (1) above.

This solution is then treated in a manner identical to that described above for the preparation of compound (2), except that the aspartic acid is replaced by the equivalent amount of iminodiacetic acid. The compound of formula (3) obtained exhibits the following elemental analysis for $C_{44}H_{36}N_{12}Na_6O_{16}S_2 \cdot 16H_2O$: calculated: C 35.68%. H 4.75%, N 11.35%, S 4.33%; found: C 35.52%, H 4.59%, N 11.27%, S 4.43%.

EXAMPLE 3

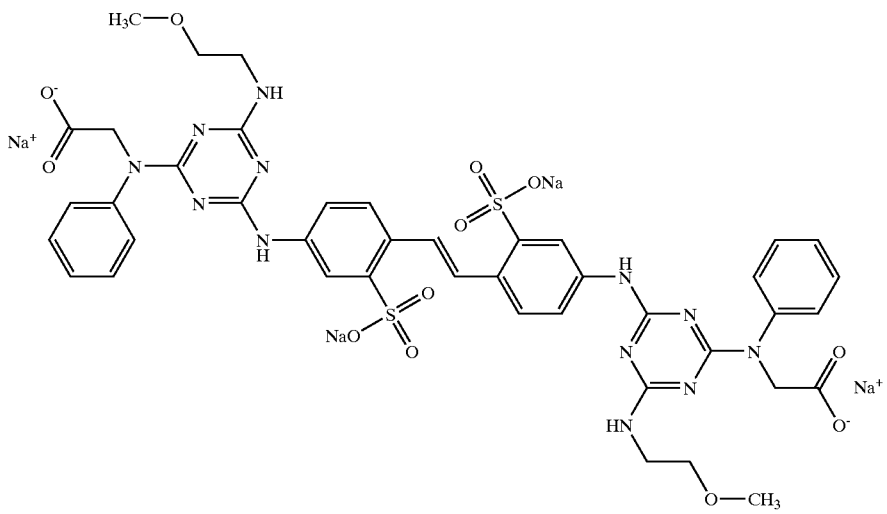
(4).

16 g of cyanuric chloride are dissolved in 90 ml of acetone and the solution poured onto 90 g of ice/water. A solution of 20 g of 80.8% 4,4'-diamino-2,2'-stilbene disulphonic acid in 200 ml of water and 90 g of ice/water is then added to the cyanuric chloride suspension over 20 minutes. The pH is adjusted to 4.5–5.0 by the addition of 43.5 ml of an aqueous 1M sodium carbonate solution, the temperature being maintained below 5° C. After stirring for 30 minutes, 13.6 g. of 97% N-phenylglycine and 43.5 ml of an aqueous 1M sodium carbonate solution are added. The mixture is then stirred for 3 hours during which time the temperature rises to 20° C., the pH being maintained at 6.8–7.5 by the addition of 10.9 g of 32% aqueous sodium hydroxide solution. The reaction mixture is filtered, the filtrate concentrated, diluted with 200 ml of methanol and the solution poured into 1 l of isopropanol. The precipitated product is separated by filtration and dried under vacuum at 80° C. yielding the compound of formula

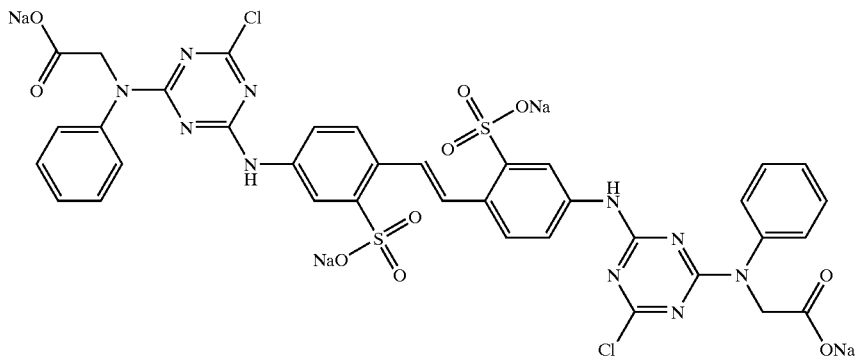

(3a)

The product obtained exhibits the following elemental analysis for $C_{36}H_{24}Cl_2N_{10}Na_4O_{10}S_2 \cdot 7H_2O \cdot 0.2NaCl$: calculated: C 38.50%, H 3.45%, Cl 6.95%, N 12.50%, S 5.71%; found: C 38.46%, H 3.60%, Cl 7.01%, N 12.59%, S 5.67%.

5.5 g of the compound (3a) are stirred in 20 ml of water and 1 g of 98% 2-methoxy-ethylamine is added. The mixture is heated to 85° C. while maintaining the pH at 8.5–9.0 by the addition of 1.1 g of 32% aqueous sodium hydroxide solution. After 2 hours the mixture is cooled, the pH adjusted to 3.0 by the addition of 2N hydrochloric acid and 50 ml of acetone added. The suspension is filtered, the solid added to 50 ml of methanol and a 32% methanolic solution of sodium methylate added to pH 9.3. The alcohol is then evaporated and the final product dried under vacuum at 80° C. to yield compound (4).

The product obtained exhibits the following elemental analysis for $C_{42}H_{36}N_{12}Na_4O_{12}S_2 \cdot 7.8H_2O \cdot 0.4NaCl$: calculated: C 41.20%, H 4.60%, Cl 1.10%. N 13.70%, S 5.23%; found: C 41.25%, H 4.47%, Cl 1.07%, N 13.78%, S 5.20%.

EXAMPLE 4

Bleached cotton swatches are treated by the exhaust method in an aqueous bath having the following composition:

0.2% of Compound (4) as 100% active substance, based on the weight of the fibre,
0.5 ml/l Ultravon® UV,
20 ml/l 3% aqueous sodium hydroxide solution,
2 ml/l 10% aqueous water glass solution and
3 ml/l 35% aqueous hydrogen peroxide solution.

The treatment is conducted at a liquor ratio of 1:40 for 30 minutes at from 25 to 95° C., then for a further 30 minutes at 95° C. and, finally cooled to 30° C. The swatches are removed from the treatment bath, rinsed and dried in an oven at 60° C.

The whiteness of the swatches is measured according to the method of Ganz, which is described in detail in The Ciba-Geigy Review, 1973/1 and also in the article "Whiteness Measurement", ISCC Conference on Fluorescence and the Colorimetry of Fluorescent Materials, Williamsberg, February 1972, published in the Journal of Color and Appearance, 1, No. 5 (1972).

The whiteness value measured for the swatches treated as described is 127.

What is claimed is:
1. A compound having the formula:

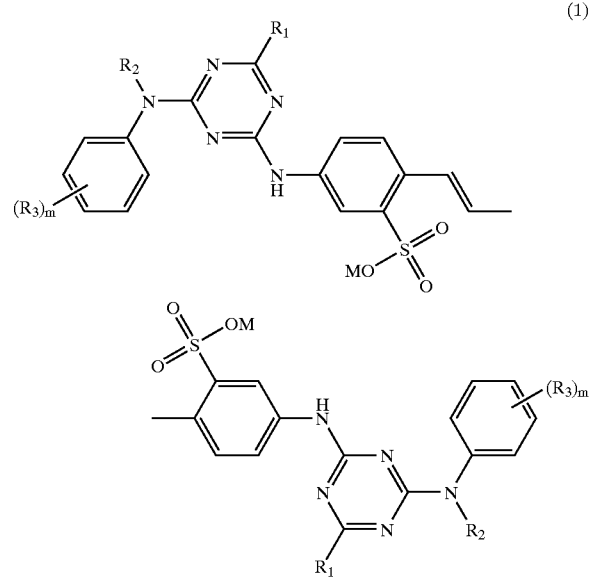

(1)

wherein each
$R_1$ represents, independently, a 2-methoxyethylamino group or an amino acid group from which a hydrogen atom on the amino group has been removed; each
$R_2$ represents, independently, methylene, ethylene or propylene residue which is substituted by hydroxy, $C_1$–$C_4$- alkyl, $C_1$–$C_4$-hydroxy- or alkoxy-alkoxy, —OCOM, —OCO$C_1$–$C_4$-alkyl, —$CO_2$M, —$CO_2C_1$–$C_4$-alkyl $SO_3$M or phenoxy which is unsubstituted or substituted by halogen, $C_1$–$C_4$-alkyl or $C_1$–$C_4$-alkoxy, —$CO_2$M or —$CO_2C_1$–$C_4$-alkyl $NH_2$ or mono- or disubstituted amino; or phenyl which is unsubstituted or substituted by 1 to 3 —$SO_3$M, —$SO_2$NH$C_1$–$C_4$-alkyl, —$SO_2NH_2$, —$CO_2$M, —$CO_2C_1$–$C_4$-alkyl, —$CONH_2$, —CONH$C_1$–$C_4$-alkyl, —NHCO$C_1$–$C_4$-alkyl or mono- or disubstituted amino groups; each $R_3$ represents, independently, hydrogen, $C_1$–$C_4$-alkyl, halogen, cyano, —$SO_2$M, —$SO_2NH_2$, $SO_2$NH$C_1$–$C_4$-alkyl, —$CO_2$M, —$CO_2C_1$–$C_4$-alkyl, —$CONH_2$, —CONH$C_1$–$C_4$-alkyl, or —NHCO$C_1$–$C_4$-alkyl;

M is hydrogen, an alkali metal atom, ammonium or a cation formed from an amine and m is an integer of 1 to 3.

2. A compound according to claim 1 in which both of the $R_1$ groups, the $R_2$ groups and the $R_3$ groups are identical.

3. A compound according to claim 2 in which each $R_4$ is an amino acid group and each has the formula —NH—CH($CO_2$H)—$R_4$ in which $R_4$ is hydrogen or a group having the formula —CHR$_5$R$_6$ in which $R_5$ and $R_6$, independently, are hydrogen or $C_1$–$_4$-alkyl optionally substituted by one or two substituents selected from hydroxy, thio, methylthio, amino, carboxy, sulfo, phenyl, 4-hydroxyphenyl, 3,5-diiodo-4-hydroxyphenyl, β-indolyl, β-imidazolyl and NH═C(NH$_2$)NH—.

4. A compound according to claim 3 in which the amino acid from which the amino acid group $R_1$ is derived is glycine, alanine, sarcosine, serine, cysteine, phenylalanine, tyrosine (4-hyroxyphenylalanine), diiodotyrosine, tryptophan (β-indolyalanine), histidine ((β-imidazolylalanine), α-aminobutyric acid, methionine, valine (α-aminoisovaleric acid), norvaline, leucine (α-aminoisocaproic acid), isoleucine (α-amino-β-methylvaleric acid), norleucine (α-amino-n-caproic acid), arginine, ornithine (α,δ-diaminovaleric acid), lysine (α,ϵ-diaminocaproic acid), aspartic acid (aminosuccinic acid), glutamic acid (α-aminoglutaric acid), threonine, hydroxyglutamic acid or taurine, or the $R_1$ groups are derived from mixtures or optical isomers of said amino acids.

5. A compound according to claim 4 in which the amino acid from which the amino acid group $R_1$ is derived is sarcosine, taurine, glutamic acid or aspartic acid.

6. A compound according to claim 1 in which the amino acid from which each amino acid group $R_1$ is derived is aspartic acid or iminodiacetic acid.

7. A compound according to claim 1 in which $R_2$ is hydroxyethyl, hydroxypropyl, ethoxyethyl, hydroxyethoxyethyl, methoxyethoxyethyl, the group —$CH_2CO_2$H or —$CH_2CH_2CO_2$H or methyl or ethyl esters thereof, the group —$CH_2$OC(═O)$CH_3$ or —$CH_2$OC(═O)$C_2H_5$, dimethylaminoethyl or ethyl sulphonic acid or the sodium salt thereof.

8. A compound according to claim 7 in which $R_2$ is hydroxyethyl or the group —$CH_2$C(═O)O$^-$Na$^+$.

9. A compound according to claim 1 in which each $R_2$ is phenyl which is unsubstituted or substituted by 1 to 3 $SO_3$M, $SO_2$NH$C_1$–$C_4$-alkyl, —$SO_2NH_2$, —$CO_2$M, —$CO_2C_1$–$C_4$-alkyl, —$CONH_2$, —CONH$C_1$–$C_4$-alkyl, —NHCO$C_1$–$C_4$-alkyl or m no- r disubstituted amino groups, wh rein M is as defined in claim 1.

10. A compound according to claim 9 in which each $R_2$ is phenyl which is unsubstituted or substituted by one $SO_3$M, —$SO_2NH_2$ or —NHCO$C_1$–$C_4$-alkyl group.

11. A compound according to claim 9 in which each $R_2$ is phenyl.

12. A compound according to claim 1 in which $R_3$ residue represents hydrogen, $C_1$–$C_4$-alkyl, halogen, cyano, $SO_3$M, —$SO_2NH_2$, $SO_2$NH$C_1$–$C_4$-alkyl, —$CO_2$M, —$CO_2C_1$–$C_4$-alkyl, —$CONH_2$, —CONH$C_1$–$C_4$-alkyl, or —NHCO$C_1$–$C_4$-alkyl, M being defined as in claim 1 and m is 1.

13. A compound according to claim 12 in which $R_3$ represents hydrogen.

14. A compound according to claim 1 in which M is hydrogen, Na, K, Ca, Mg, ammonium, mono-, di-, tri- or tetra-$C_1$–$C_4$alkylammonium, mono-, di- or tri-$C_1$–$C_4$-hydroxyalkylammonium or ammonium that is di- or tri-substituted with a mixture of $C_1$–$C_4$-alkyl and $C_1$–$C_4$-hydroxyalkyl groups.

15. A compound according to claim 14 in which each M is hydrogen or Na.

16. A compound of formula 1 according to claim 1 in which:

$R_1$ is an amino acid group derived from aspartic acid or iminodiacetic acid, $R_2$ is hydroxyethyl, $R_3$ is hydrogen and M is sodium.

17. A compound of the formula 1 in which:

$R_1$ is a 2-methoxyethylamino group, $R_2$ is the group —$CH_2$C(═O)O$^-$Na$^+$, $R_3$ is hydrogen and M is sodium.

18. A compound of the formula:

(5)

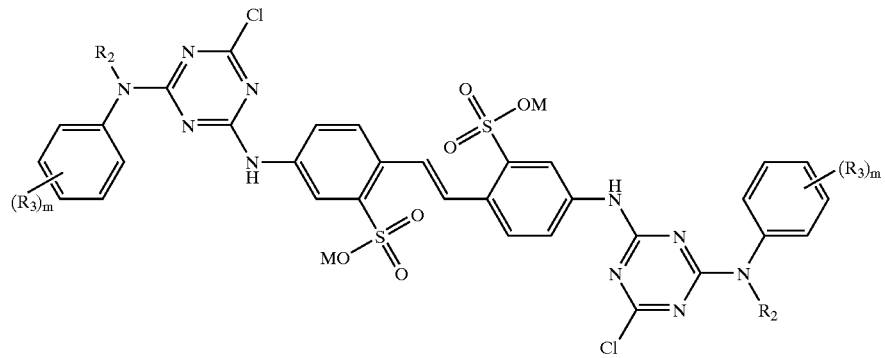

in which $R_2$, $R_3$, M and m are as defined in claim 1.

19. A process for the preparation of a compound of the formula (1) according to claim 1, which comprises reacting the compound of formula

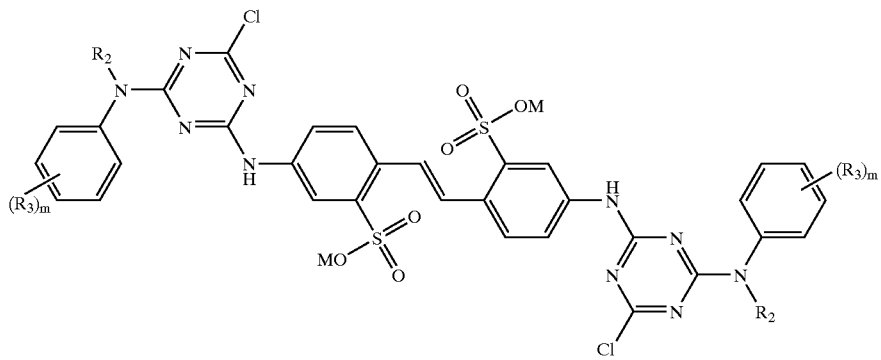

(5)

with a compound capable of introducing a group $R_1$ in place of Cl, in which $R_1$, $R_2$, $R_3$, M and m are as defined in claim 1.

20. A process for the preparation of a compound of formula (1) according to claim 1 by reacting, under known reaction conditions, cyanuric chloride, successively, in any desired sequence, with each of 4,4'-diamino-2,2'-stilbene disulphonic acid, an amino compound capable of introducing a group

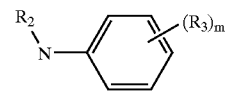

in which $R_2$, $R_3$, and m have their previous significance, and a compound capable of introducing a group $R_1$, in which $R_1$ is defined in claim 1.

* * * * *